US012606519B2

(12) United States Patent
Turchetta et al.

(10) Patent No.: US 12,606,519 B2
(45) Date of Patent: Apr. 21, 2026

(54) PROCESS FOR PREPARING {6-[(DIETHYLAMINO) METHYL]NAPHTHALEN-2-YL}METHYL [4-(HYDROXYCARBAMOYL)PHENYL] CARBAMATE HAVING HIGH PURITY

(71) Applicant: ITALFARMACO SPA, Milan (IT)

(72) Inventors: Stefano Turchetta, Rome (IT); Maurizio Zenoni, Ferentino (IT); Elio Ullucci, Latina (IT); Stefania Cocciolo, Patrica (IT); Giorgio Berardi, Ripi (IT); Nakia Maulucci, Alatri (IT)

(73) Assignee: ITALFARMACO SPA, Milano MI (IT)

(*) Notice: Subject to any disclaimer, the term of this patent is extended or adjusted under 35 U.S.C. 154(b) by 59 days.

(21) Appl. No.: 18/338,435

(22) Filed: Jun. 21, 2023

(65) Prior Publication Data

US 2023/0348368 A1 Nov. 2, 2023

Related U.S. Application Data

(62) Division of application No. 17/435,731, filed as application No. PCT/IB2020/051907 on Mar. 5, 2020, now Pat. No. 12,129,224.

(30) Foreign Application Priority Data

Mar. 6, 2019 (IT) ........................ 102019000003281

(51) Int. Cl.

| | |
|---|---|
| ***C07C 271/28*** | (2006.01) |
| ***B01J 20/286*** | (2006.01) |

(Continued)

(52) U.S. Cl.

CPC ........... *C07C 271/28* (2013.01); *B01J 20/286* (2013.01); *C07C 269/06* (2013.01); *C07C 269/08* (2013.01); *G01N 2030/027* (2013.01)

(58) Field of Classification Search

None

See application file for complete search history.

(56) References Cited

U.S. PATENT DOCUMENTS

| | | |
|---|---|---|
| 6,034,096 A | 3/2000 | Bertolini |
| 7,329,689 B2 | 2/2008 | Pinori |
| 8,518,988 B2 | 8/2013 | Turchetta |

FOREIGN PATENT DOCUMENTS

| | | |
|---|---|---|
| WO | WO 8028840653 | 5/2004 |

OTHER PUBLICATIONS

European Medicines Agency ("Note for Guidance on Impurities in New Drug Products" (CPMP/ICH/2738/99), Jun. 2006) (Year: 2006).*

(Continued)

*Primary Examiner* — Amy C Bonaparte

(74) *Attorney, Agent, or Firm* — HUESCHEN AND SAGE

(57) ABSTRACT

A process for obtaining {{6-[(diethylamino)methyl]naphthalen-2-yl}methyl [4-(hydroxycarbamoyl)phenyl]carbamate and/or pharmaceutically acceptable salts thereof having high purity is described. This process allows to obtain a product having an amount of any single unknown impurity equal to or less than 0.10%, as well as a product having a purity greater than 99.5%, preferably equal to or greater than 99.6%.

An HPLC method for determining the purity of the product and possible impurities thereof is also described.

10 Claims, 1 Drawing Sheet

(51) Int. Cl.

| | |
|---|---|
| ***C07C 269/06*** | (2006.01) |
| ***C07C 269/08*** | (2006.01) |
| *G01N 30/02* | (2006.01) |

(56) References Cited

OTHER PUBLICATIONS

Furlan, Antonio, et al., "Pharmacokinetics, safety and inducible cytokine responses during a phase 1 trial of the oral histone deacetylase inhibitor ITF2357 (Givinnstat)", Mol Med, 17(5-6), May-Jun. 2011, pp. 353-362.

International Search Report for FCT/IB2020/051907 dated Jun. 12, 2020.

Italian Partial Search Report for IT201900063281 dated Oct. 30, 2019.

English Abstract of Wen, et al., Journal of Shenyang Pharmaceutical University, 2018, 35, 845-850.

Wen, et al., Journal of Shenyang Pharmaceutical University, 2018, 35, 845-850.

* cited by examiner

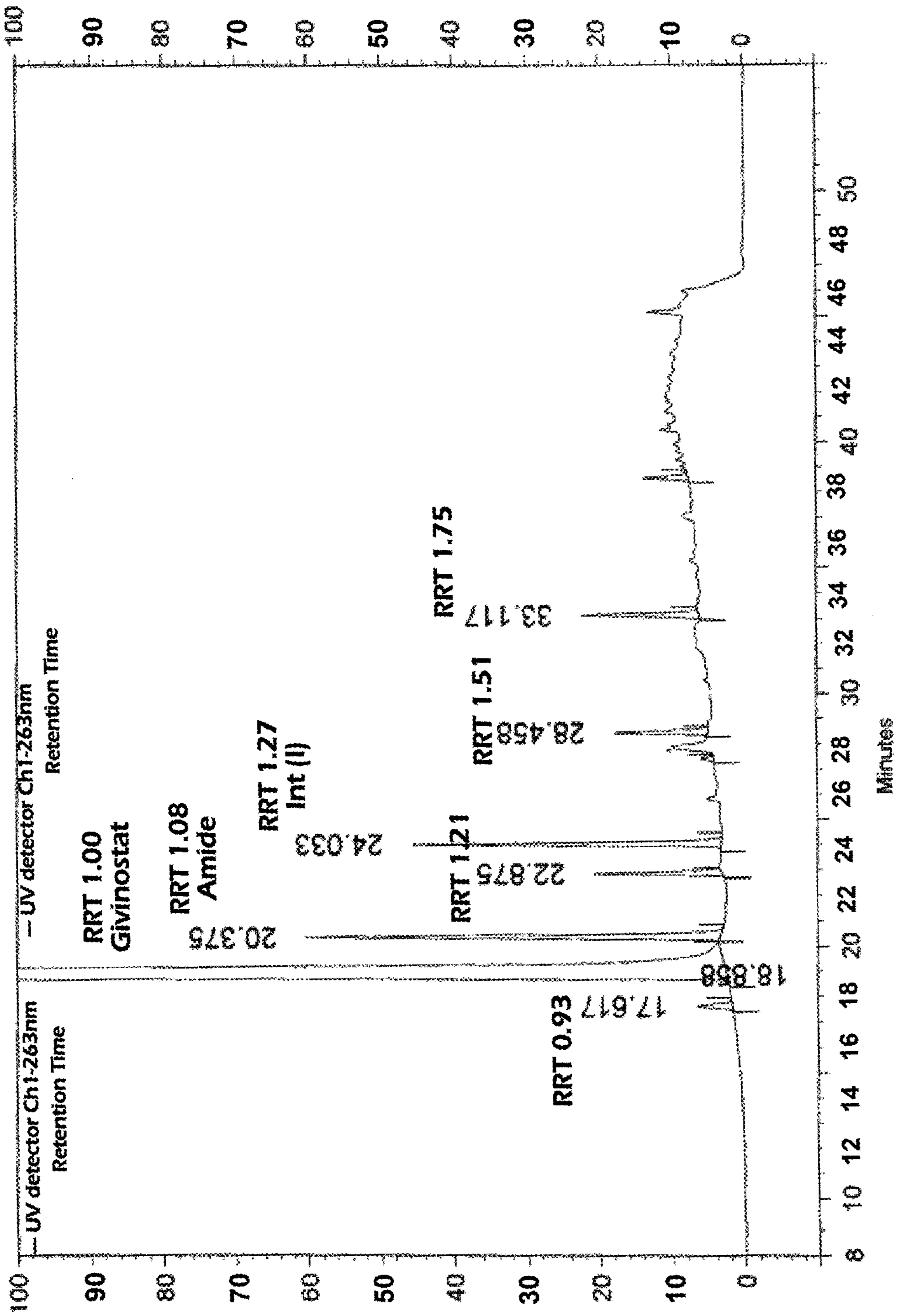
UV detector Ch1-263nm
Retention Time
RRT 0.93
17.617
18.858
RRT 1.00
Givinostat
20.375
RRT 1.08
Amide
RRT 1.21
22.875
24.033
RRT 1.27
Int (I)
RRT 1.51
28.458
RRT 1.75
33.117
Minutes

PROCESS FOR PREPARING {6-[(DIETHYLAMINO) METHYL]NAPHTHALEN-2-YL}METHYL [4-(HYDROXYCARBAMOYL)PHENYL] CARBAMATE HAVING HIGH PURITY

The object of the present invention is a process for obtaining {6-[(diethylamino)methyl]naphthalen-2-yl}methyl [4-(hydroxycarbamoyl)phenyl]carbamate and/or pharmaceutically acceptable salts thereof having high purity. Such process allows to obtain a product having an amount of any single unknown impurity equal to or less than 0.10%, as well as a product having a purity greater than 99.5%, preferably equal to or greater than 99.6%.

A further object of the present invention is an HPLC method for determining the purity of the product and possible impurities thereof.

STATE OF THE ART

Givinostat®, also known by the name of ITF2357, (IUPAC name {6-[(diethylamino)methyl]naphthalen-2-yl}methyl [4-(hydroxycarbamoyl)phenyl]carbamate is a hydroxamic acid, used in the form of hydrochloride thereof, in particular hydrochloride monohydrate, that acts as an inhibitor of Histone Deacetylase (HDAC) and exerts its action on the homonymous class I and II enzymes.

Givinostat shows a very promising activity profile in multiple myeloma and acute myelogenic leukemia, both in vitro and in vivo, and also acts as an anti-inflammatory agent and as an inhibitor of tumor necrosis factor alpha (TNF-α), IL-1, and IL-6 secretion.

Givinostat is currently used in multiple Phase III studies for inflammatory diseases (Duchenne and Becker muscular dystrophy, juvenile arthritis, and polycythemia vera) and in clinical trials for blood cancers (myelomas and lymphomas).

U.S. Pat. No. 6,034,096 reports the preparation of Givinostat, while U.S. Pat. No. 7,329,689 and WO2004/065355 deal with the preparation and characterization of one polymorph monohydrate thereof.

U.S. Pat. No. 8,518,988 describes the preparation and characterization of an anhydrous polymorph of Givinostat.

The methods for preparing Givinostat described in the cited documents first provide for the synthesis of the acyl chloride (II) from intermediate (I) (STEP 1), which is then added as THF-wet solid to a solution of hydroxylamine in water and THF to generate the final product (STEP 2), according to the following Scheme 1:

Scheme 1

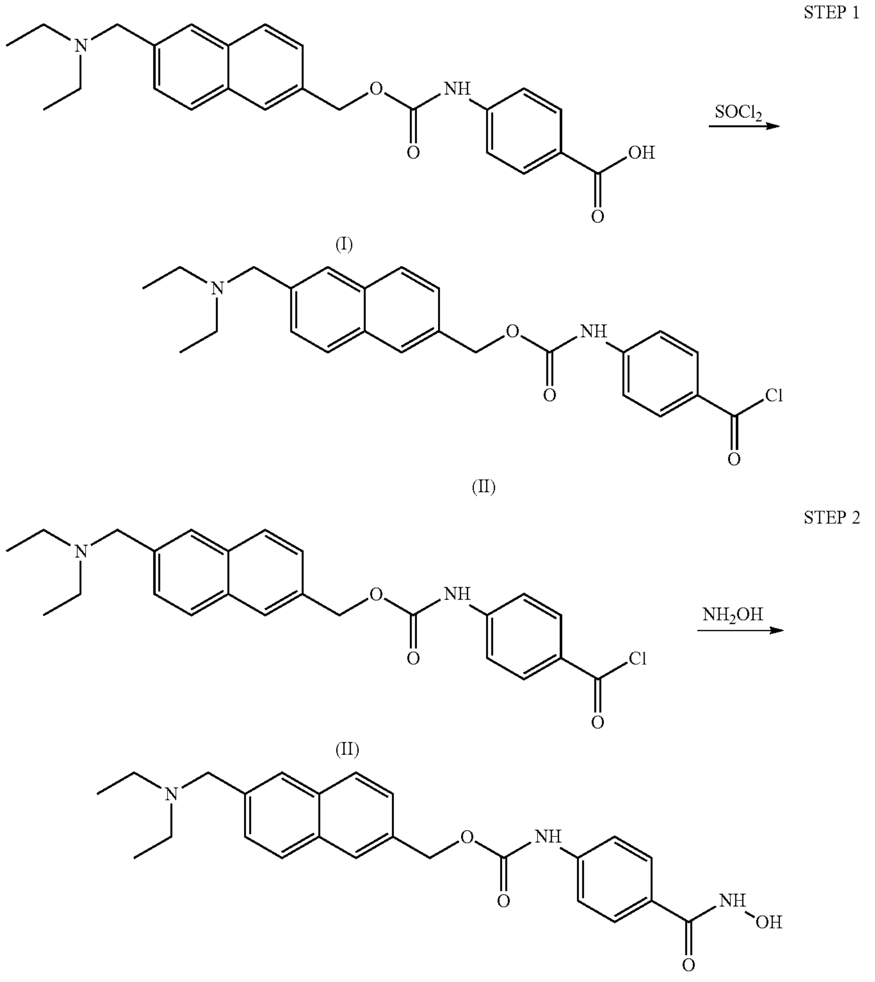

(I)

(II)

(II)

GIVINOSTAT

The above cited documents do not describe any impurities deriving from the synthesis.

The literature (A. Furlan, V. Monzani, L. L. Reznikov, F. Leoni, G. Fossati. D. Modena, P. Mascagni, C. A. Dinarello, *Mol. Med.* 2011, 17 (5-6) 353-362) elucidates that intermediate (I) (ITF2375) and the corresponding amide (ITF2374) are the two main in vivo metabolites of Givinostat (ITF2357), deriving from biotransformation of the hydroxamic group into carboxylic acid and amide, respectively.

The amide (ITF2374) has the following formula (Ia):

(Ia)

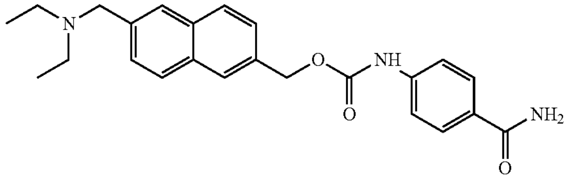

Therefore, the presence of intermediate (I) or amide (la) in Givinostat, in amounts greater than 0.15% is justified, those being qualified impurities.

On the basis of current guidelines in the pharmaceutical field, which provide for a detailed description of the impurity profile of active ingredients intended for human use, the development of new processes for producing Givinostat in accordance with current quality standards and the identification of new analytical techniques for determining the purity of Givinostat, such as to allow the identification of the presence of any impurities, is of fundamental importance.

Definitions

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference; thus, the inclusion of such definitions herein should not be construed to represent a substantial difference over what is generally understood in the art.

The term "physiologically acceptable excipient" herein refers to a substance devoid of any pharmacological effect of its own and which does not produce adverse reactions when administered to a mammal, preferably a human. Physiologically acceptable excipients are well known in the art and are disclosed, for instance in the *Handbook of Pharmaceutical Excipients*, sixth edition 2009, herein incorporated by reference.

The term "pharmaceutically acceptable salts" refers to those salts having the biological efficacy and properties of the salified compound and which do not produce adverse reactions when administered to a mammal, preferably a human being. The pharmaceutically acceptable salts can be inorganic or organic salts; examples of pharmaceutically acceptable salts include, but are not limited to, carbonate, hydrochloride, hydrobromide, sulfate, hydrogen sulfate, citrate, maleate, fumarate, trifluoroacetate, 2-naphthalenesulfonate, and para-toluenesulfonate. More information on pharmaceutically acceptable salts may be found in *Handbook of pharmaceutical salts*, P. Stahl, C. Wermuth, WILEY-VCH, 127-133, 2008, incorporated herein by reference.

The terms "comprising", "having", "including" and "containing" are to be construed open-ended terms (i.e. meaning "including, but not limited to") and are to be considered as providing support also for terms as "consist essentially of", "consisting essentially of", "consist of" or "consisting of". The terms "consist essentially of", "consisting essentially of" are to be construed as semi-closed terms, meaning that no other ingredients which materially affects the basic and novel characteristics of the invention are included (optional excipients may thus included).

The terms "consists of", "consisting of" are to be construed as closed terms. The term "having high purity" refers to a purity greater than 99.5%, preferably equal to or greater than 99.6%.

Within the scope of the present description, the terms Givinostat or ITF2357 are intended to indicate the hydrochloride salt of {6-[(diethylamino)methyl]naphthalen-2-yl}methyl [4-(hydroxycarbamoyl)phenyl]carbamate, in particular hydrochloride monohydrate (CAS n. 732302-99-7). The hydrochloride salt has instead a CAS number of 199657-29-9 and the free base has a CAS number of 497833-27-9.

The term "halogen" refers to fluorine (F), chlorine (Cl), bromine (Br), or iodine (I).

The term "dipolar aprotic solvent not sensitive to acidity" refers to a solvent devoid of acid sensitive components. THF is an example of an acid sensitive solvent. DMSO, acetonitrile, dimethylacetamide, or dimethylformamide are instead examples of solvents not sensitive to acidity.

The term "unknown impurity" refers to any unknown impurity present in {6-[(diethylamino)methyl]naphthalen-2-yl}methyl [4-(hydroxycarbamoyl)phenyl]carbamate and/or pharmaceutically acceptable salts thereof.

BRIEF DESCRIPTION OF THE INVENTION

With reference to processes for the preparation of Givinostat used in the state of the art, the inventors have observed that these processes provide Givinostat having a single unknown impurity content greater than 0.10%.

The Applicant therefore faced the problem of developing a new process to prepare Givinostat having a content of any single unknown impurity equal to or lower than 0.10% (area % in the HPLC chromatogram), which is the level expected by ICH for unknown impurities, when the daily dosage of the active substance is less than 2 g, as in the case of Givinostat.

Unexpectedly, it has been found that in STEP 1 (Scheme 1), it is critical to perform the halogenation reaction of intermediate (I) in a solvent devoid of acid sensitive components to reduce the halogenating agent equivalents necessary to complete the desired reaction, while obtaining intermediate (II) having an amount of impurities lower than that obtained by applying the known art.

Equally unexpectedly, the inventors found that, in STEP 2 (Scheme 1), intermediate (II) and hydroxylamine order of addition is critical to obtain a final product having a single unknown impurity equal to or lower than 0.10% by area in the relative purity analysis chromatogram.

Therefore, in a first aspect, the present invention relates to a process for preparing {6-[(diethylamino)methyl]naphthalen-2-yl}methyl [4-(hydroxycarbamoyl)phenyl]carbamate and/or pharmaceutically acceptable salts thereof having an amount of any single unknown impurity equal to or lower than 0.10% and/or high purity.

In a preferred embodiment, the process of the present invention allows to obtain {6-[(diethylamino)methyl]naphthalen-2-yl}methyl [4-(hydroxycarbamoyl)phenyl]carbamate and/or pharmaceutically acceptable salts thereof having a purity greater than 99.5%, preferably equal to or greater than 99.6%.

According to a second aspect thereof, the present invention relates to {6-[(diethylamino)methyl]naphthalen-2-yl}methyl [4-(hydroxycarbamoyl)phenyl]carbamate and/or pharmaceutically acceptable salts thereof, preferably hydrochloride, more preferably hydrochloride monohydrate, having an amount of any single unknown impurity equal to or lower than 0.10% or having an amount of any single impurity other than intermediate (I) or amide (la) equal to or lower than 0.15%, preferably equal to or lower than 0.10%.

According to a third aspect thereof, the present invention relates to {6-[(diethylamino)methyl]naphthalen-2-yl}methyl [4-(hydroxycarbamoyl)phenyl]carbamate and/or pharmaceutically acceptable salts thereof, preferably hydrochloride, more preferably hydrochloride monohydrate, having a purity greater than 99.5%, preferably equal to or greater than 99.6%.

According to a fourth aspect thereof, the present invention relates to a new HPLC analytical method for determining the purity of {6-[(diethylamino)methyl]naphthalen-2-yl}methyl [4-(hydroxycarbamoyl)phenyl]carbamate and/or pharmaceutically acceptable salts thereof and detect impurities thereof.

According to a fifth aspect thereof, the present invention relates to {6-[(diethylamino)methyl]naphthalen-2-yl}methyl [4-(hydroxycarbamoyl)phenyl]carbamate and/or pharmaceutically acceptable salts thereof, preferably hydrochloride, more preferably hydrochloride monohydrate, having an amount equal to or lower than 0.10% of an unknown impurity at an RRT of 0.93±0.02 and/or an unknown impurity at an RRT of 1.21±0.02 and/or an unknown impurity at an RRT of 1.51±0.02 and/or of an unknown impurity at an RRT 1.75±0.02, the RRT being measured using the HPLC method according to the invention.

According to a sixth aspect thereof, the present invention relates to a process for preparing {6-[(diethylamino)methyl]naphthalen-2-yl}methyl [4-(hydroxycarbamoyl)phenyl]carbamate and/or pharmaceutically acceptable salts thereof comprising the HPLC method for determining the purity according to the invention.

DESCRIPTION OF THE FIGURES

The FIGURE shows the chromatogram obtained by the HPLC method according to the invention, on an ad hoc prepared mixture containing all the typical Givinostat impurities.

DETAILED DESCRIPTION OF THE INVENTION

An object of the present invention is a process for preparing {6-[(diethylamino)methyl]naphthalen-2-yl}methyl [4-(hydroxycarbamoyl)phenyl]carbamate and/or pharmaceutically acceptable salts thereof having an amount of any single unknown impurity equal to or lower than 0.10%, said process comprising the steps of:

i) preparing a solution or a suspension of the compound of formula (II) in an organic solvent:

(II)

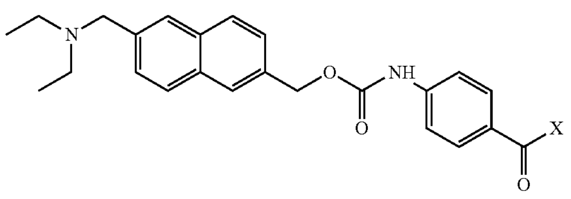

wherein X is halogen, preferably chlorine;

ii) adding hydroxylamine to the solution or suspension obtained from step i).

Within the scope of the present description, steps i) and ii) will be named STEP 2 according to the process of the invention.

In a preferred embodiment, the organic solvent of step i) in STEP 2 is selected from the group comprising THF, methyl-THF, dioxane, ethylene glycol dimethyl ether, and bis(2-methoxyethyl)ether.

Preferably, said organic solvent is used in an amount comprised between 1 and 100 parts by volume per part by weight of the compound of formula (II). Preferably, said organic solvent has a water content lower than 0.5%. Preferably, step ii) in STEP 2 of the process according to the invention is carried out at room temperature.

In a preferred embodiment, the process of the present invention (STEP 2) is characterized in that it further comprises a step iii) of isolating {6-[(diethylamino)methyl]naphthalen-2-yl}methyl [4-(hydroxycarbamoyl)phenyl]carbamate as a free base or as a pharmaceutically acceptable salt, preferably hydrochloride, more preferably hydrochloride monohydrate.

In a further preferred embodiment, the compound of formula (II) is obtained from the corresponding acid of formula (I) by reaction with a halogenating agent, preferably a chlorinating agent (step a), in an aprotic dipolar solvent insensitive to acidity.

Preferably, the compound of formula (II) is isolated from the reaction mixture by precipitation with organic solvent, preferably followed by filtration (step b). Within the scope of the present description, steps a) and b) will be named STEP 1 according to the process of the invention.

The solvent insensitive to acidity is a solvent devoid of acid sensitive components (therefore devoid of THF for example). This characteristic of the solvent allows to use reduced amounts of halogenating agent compared to the prior art.

By way of example, THF represents an acid-sensitive solvent, since in acidic conditions it can degrade and generate reactive species that can form unwanted by-products in the halogenation reaction.

Preferably, in step a) of STEP 1, said aprotic dipolar solvent insensitive to acidity is selected from DMSO, acetonitrile, dimethylacetamide, or dimethylformamide, more preferably dimethylformamide.

Examples of chlorinating agents that may be used in the process of the present invention are thionyl chloride ($SOCl_2$), phosphorus trichloride ($PCl_3$), phosphorus oxychloride ($POCl_3$), or phosphorus pentachloride ($PCl_5$). Alternatively, the corresponding brominating agents $SOBr_2$, $PBr_3$, $POBr_3$ or $PBr_5$ may be used.

In a preferred embodiment of step b) in STEP 1, the organic solvent used to precipitate the compound (II) is selected from aliphatic or aromatic hydrocarbons, ethers, esters or alcohols, more preferably toluene or THF.

A further object of the present invention is {6-[(diethylamino)methyl]naphthalen-2-yl}methyl [4-(hydroxycarbamoyl)phenyl]carbamate and/or pharmaceutically acceptable salts thereof having an amount of any single unknown impurity equal to or lower than 0.10%, obtainable by application with respect to the known art only of STEP 2 as defined above.

In a further preferred embodiment, the present invention relates to {6-[(diethylamino)methyl]naphthalen-2-yl}methyl [4-(hydroxycarbamoyl)phenyl]carbamate and/or pharmaceutically acceptable salts thereof having a purity greater than 99.5%, preferably equal to or greater than 99.6%, by application with respect to the known art of both STEP 1 and STEP 2 as defined above.

A further object of the present invention is {6-[(diethylamino)methyl]naphthalen-2-yl}methyl [4-(hydroxycarbamoyl)phenyl]carbamate and/or pharmaceutically acceptable salts thereof, preferably hydrochloride, more preferably hydrochloride monohydrate, having an amount of any single unknown impurity equal to or lower than 0.10% or having an amount of any single impurity other than intermediate (I) or amide (la) equal to or lower than 0.15%, preferably equal to or lower than 0.10%.

A further object of the present invention is {6-[(diethylamino)methyl]naphthalen-2-yl}methyl [4-(hydroxycarbamoyl)phenyl]carbamate and/or pharmaceutically acceptable salts thereof, preferably hydrochloride, more preferably hydrochloride monohydrate, having a purity greater than 99.5%, preferably equal to or greater than 99.6%.

A further object of the present invention is {6-[(diethylamino)methyl]naphthalen-2-yl}methyl [4-(hydroxycarbamoyl)phenyl]carbamate and/or pharmaceutically acceptable salts thereof, preferably hydrochloride, more preferably hydrochloride monohydrate, having an amount equal to or lower than 0.10% of an unknown impurity at an RRT of 0.93±0.02 and/or an unknown impurity at an RRT of 1.21±0.02 and/or an unknown impurity at an RRT of 1.51±0.02 and/or an unknown impurity at an RRT 1.75±0.02, the RRT being measured using the HPLC method according to the invention.

In a preferred embodiment, the RRT is measured using the following HPLC method:

Stationary phase: support based on silica particles containing C18 alkyl chains and having a carbon load lower than 9% by weight;

Mobile phase A: Water buffered at pH 3.7-3.8

Mobile phase B: Methanol buffered at pH 3.7-3.8 using the following gradient elution method:

| Time (min) | Eluent A % (v/v) | Eluent B % (v/v) |
|---|---|---|
| 0 | 75 | 25 |
| 5 | 75 | 25 |
| 35 | 10 | 90 |
| 40 | 10 | 90 |
| 40.1 | 75 | 25 |
| 50 (end run) | 75 | 25, |

Preferably, an ammonium formate-formic acid buffer at pH 3.7-3.8 is used.

Preferably, a 263 nm UV detector is used.

Preferably, the column temperature is 25±1° C.

Preferably, the injection volume is 5 μL.

Preferably, the flow rate is 0.25 mL/min.

Preferably, the product sample is diluted in DMSO.

A further object of the present invention is a pharmaceutical composition containing {6-[(diethylamino)methyl]naphthalen-2-yl}methyl [4-(hydroxycarbamoyl)phenyl]carbamate and/or pharmaceutically acceptable salts thereof, as defined above, and at least one pharmaceutically acceptable excipient.

In a preferred embodiment of the pharmaceutical composition, the active principle is in the form of micronized particles, having an average size smaller than 200 μm, preferably between 100 μm and 1 μm, more preferably between 50 μm and 5 μm.

A further object of the present invention is also a method for determining the purity of the product {6-[(diethylamino)methyl]naphthalen-2-yl}methyl [4-(hydroxycarbamoyl)phenyl]carbamate and/or pharmaceutically acceptable salts thereof comprising eluting the product through an HPLC column having a stationary phase containing alkyl chains bound to an inorganic support, for example silica, and subsequent detection of the same product and impurities thereof using a detector suitable for measuring the amount of analyte eluting from the column, for example a detector of the UV, MS or RID type.

In a preferred embodiment of the process according to the invention, said alkyl chains are of octadecyl, octyl or butyl (C18, C8 or C4) type, preferably C18. In one even more preferred embodiment, the stationary phase consists of a silica support, derivatized with C18 alkyl chains, having a carbon load lower than 9% by weight.

Carbon load means the carbon content, as % by weight, of the stationary phase bound to silica. High carbon loads (15-25%) make the surface of the stationary phase more hydrophobic and can retain the most hydrophobic impurities, making correct quantitative evaluation thereof impossible.

Several columns of this type are commercially available, for example ACE 5 C18-300, Halo C18 (solid core), YMC-Pack OSD-A, BioBasic-18 PEEK. In a preferred embodiment, a column Halo C18-90 Å (Code 95812-902 produced by Advanced Materials Technology) is used.

Different eluents selected from water, a polar organic solvent, or a mixture thereof may be used with the stationary phase and detector combinations described above. Said polar organic solvent is a C1-C4 alcohol, preferably methanol, or acetonitrile.

Preferably, in the HPLC method of the present invention mixtures of water and methanol, water and acetonitrile can be used, optionally with or without an elution gradient, optionally with or without buffers. Preferably, the aforementioned mixtures can be used with the addition of a buffer. More preferably, an ammonium formate-formic acid buffer at pH 3.7-3.8.

In a preferred embodiment, a chromatographic run according to the following scheme is used as the elution method:

| Time (min) | Eluent A % (v/v) | Eluent B % (v/v) |
|---|---|---|
| 0 | 75 | 25 |
| 5 | 75 | 25 |
| 35 | 10 | 90 |
| 40 | 10 | 90 |
| 40.1 | 75 | 25 |
| 50 (end run) | 75 | 25 |

wherein Eluent A means water and ammonium formate-formic acid buffer at pH 3.7-3.8, and Eluent B means methanol and ammonium formate-formic acid buffer at pH 3.7-3.8.

A further object of the present invention is also a process for preparing {6-[(diethylamino)methyl]naphthalen-2-yl}methyl [4-(hydroxycarbamoyl)phenyl]carbamate and/or pharmaceutically acceptable salts thereof comprising the method for determining the purity according to the invention.

The examples reported in the following experimental section are to be considered as examples of the process object of the present invention and do not constitute a limitation to the scope of validity of the invention itself.

EXPERIMENTAL PART

Example 1 (Comparative)

Synthesis of Intermediate (II) According to the Prior Art 73 g (0.1796 moles) of Intermediate (I) and 1.12 L of dry THF are charged into a 2 L reactor previously dried and under an inert atmosphere. The suspension obtained is stirred at room temperature for 30 minutes. The internal temperature is lowered to 3÷5° C., and 64 g of thionyl chloride (0.538 moles) are added over 5 minutes, then the reaction mixture is heated up to reflux temperature and kept under stirring for about 1 hour. 2 g of dry DMF are added and the mixture is stirred for further 4 hrs at the same temperature. The reaction mixture is then concentrated under reduced pressure to a residual volume of about 0.3 L. Then, 0.35 L of toluene are charged, and the mixture is concentrated again. This operation is repeated another time. After cooling the mixture to room temperature, dry THF (0.7 L) is added, and the mixture is stirred for about 30 minutes. The white precipitate of Intermediate (II) is then filtered and washed with dry THF. The wet product (107 g) is stored at 5° C. and used as it is.

Example 2 (Comparative)

Synthesis of Givinostat According to the Process of the Prior Art (Experiment TT180)

125 mL of dry THF and 60 mL of water are charged into a 1 L reactor, previously dried and under an inert atmosphere. Aqueous hydroxylamine (21 g, 50% w/w) is added to this solution, and the resulting mixture is cooled to 5° C. 19 g of wet Intermediate (II) from Example 1 (corresponding to 13 g of starting material, Intermediate (I)) are charged in a single portion and the internal temperature gradually increases to 20±3° C. Gradual dissolution is observed and the resulting mixture is kept under stirring for 30-40 minutes. Then, water (55 mL) is added and 6N HCl aqueous solution (about 60 g) is then slowly added until reaching pH<2, while keeping the internal temperature at 20±3° C. THF is then removed under reduced pressure until the total volume is about halved and a white precipitate is observed. The mixture is cooled to 10° C. and kept under stirring at this temperature for 30 minutes. The product is isolated by vacuum filtration and washed with water. 16.4 g of wet crude Givinostat are obtained.

Crude Givinostat is suspended in a solution of $NaHCO_3$ (6.5 g) in 285 mL of water at 20±3° C., then THF (265 mL) is added and gradual dissolution is observed. The resulting solution is stirred for 30 minutes, then ethyl acetate (132 mL) is added. After 15 minutes, stirring is stopped and the two phases are allowed to separate. The aqueous phase is discarded, and the organic phase is treated with 37% HCl under vigorous stirring until reaching pH<2. The resulting suspension is stirred for 30 minutes, then the precipitate is isolated by vacuum filtration and washed with THF. 17 g of wet pure Givinostat are obtained.

The product is dried in oven at 30° C. under reduce pressure for 16 hours. 7.2 g of dry pure Givinostat are obtained, whose purity is 98.8% and shows the presence of an unknown impurity at 0.23%.

Example 3

Synthesis of Givinostat According to the Process of the Prior Art for Step 1 and Process of the Invention for Step 2 (Experiment TT177)

In a 1 L reactor, previously dried and under an inert atmosphere, 29.3 g of wet Intermediate (II) from Example 1 (corresponding to 20 g of starting material Intermediate (I)) are suspended in 192 mL of dry THF and the internal temperature brought to 20±3° C. Aqueous hydroxylamine (32 g, 50% w/w) is added in a single portion and the mixture is kept under stirring for 30-40 minutes. Then, water (176 mL) is added and gradual dissolution of the precipitate is observed. 6N HCl aqueous solution (about 93 g) is slowly added until reaching pH<2, while keeping the internal temperature at 20±3° C. THF is then removed under reduced pressure until the total volume is about halved, and a white precipitate is observed. The mixture is cooled to 10° C. and kept under stirring at this temperature for 30 minutes. The product is isolated by vacuum filtration and washed with water. 29 g of wet crude Givinostat are obtained.

The wet crude Givinostat is suspended in a solution of $NaHCO_3$ (10 g) in 408 mL of water at 20±3° C., then THF (408 mL) is added and gradual dissolution is observed. The resulting solution is stirred for 30 minutes, then ethyl acetate (204 mL) is added. After 15 minutes, stirring is stopped and the two phases are allowed to separate. The aqueous phase is discarded, and the organic phase is treated with 37% HCl under vigorous stirring until reaching pH<2. The resulting suspension is stirred for 30 minutes, then the precipitate is isolated by vacuum filtration and washed with THF. 31 g of wet pure Givinostat are obtained.

The product is dried in oven at 30° C. under reduced pressure for 16 hours. 15.6 g of dry pure Givinostat are obtained. HPLC purity analysis shows that the product does not contain any unknown impurities in amounts greater than 0.10%.

Example 4

Synthesis of Givinostat According to the Process of the Prior Art for Step 1 and Process of the Invention for STEP 2 (Entry TT183)

In a 1 L reactor, previously dried and under an inert atmosphere, 29.3 g of wet Intermediate (II) from Example 1 (corresponding to 20 g of starting material Intermediate (I)) are suspended in 192 mL of dry THF and the internal temperature brought to 20±3° C. Aqueous hydroxylamine (32 g, 50% w/w) is added by pouring it over 15 minutes and the mixture is kept under stirring for 30-40 minutes. Then, water (176 mL) is added and gradual dissolution of the precipitate is observed. 6N HCl aqueous solution (about 91 g) is slowly added until reaching pH<2, while keeping the internal temperature at 20±3° C. THF is then removed under reduced pressure until the total volume is about halved and a white precipitate is observed. The mixture is cooled to 10° C. and kept under stirring at this temperature for 30 minutes. The product is isolated by vacuum filtration and washed with water. 36 g of wet crude Givinostat are obtained.

The wet crude Givinostat is suspended in a solution of $NaHCO_3$ (10 g) in 408 mL of water at 20±3° C., then THF (408 mL) is added and gradual dissolution is observed. The resulting solution is stirred for 30 minutes, then ethyl acetate (204 mL) is added. After 15 minutes, stirring is stopped and the two phases are allowed to separate. The aqueous phase is discarded, and the organic phase is treated with 37% HCl under vigorous stirring until reaching pH<2. The resulting suspension is stirred for 30 minutes, then the precipitate is isolated by vacuum filtration and washed with THF. 27 g of wet pure Givinostat are obtained.

The product is dried in oven at 30° C. under reduced pressure for 16 hours. 15.4 g of dry pure Givinostat are obtained. HPLC purity analysis shows that the product does not contain any unknown impurities in amounts greater than 0.10%.

Example 5

Synthesis of Givinostat According to the Process of the Prior Art for Step 1 and Process of the Invention for Step 2. Industrial Scale In a 2000 L reactor, previously dried and under an inert atmosphere, 50.0 kg of wet Intermediate (II) (corresponding to 40 g of starting material Intermediate (I)) are suspended in 400 L of dry THF and the internal temperature brought to 20±3° C. Aqueous hydroxylamine (67.2 kg, 50% w/w) is added by pouring it over 15 minutes and the mixture is kept under stirring for 30-40 minutes. Then, water (447 L) is added and gradual dissolution of the precipitate is observed. 6N HCl aqueous solution (about 170 kg) is slowly added until reaching pH<2, while keeping the internal temperature at 20±3° C. THF is then removed under reduced pressure until the total volume is about halved, and a white precipitate is observed. The mixture is cooled to 10° C. and kept under stirring at this temperature for 30 minutes. The product is isolated by vacuum filtration and washed with water. 60 kg of wet crude Givinostat are obtained.

The wet crude Givinostat is suspended in a solution consisting of $NaHCO_3$ (21 kg) in 860 L of water and 860 L of THF at 20±3° C., observing gradual dissolution. The resulting solution is stirred for 30 minutes, then ethyl acetate (440 L) is added. After 15 minutes, stirring is stopped and the two phases are allowed to separate. The aqueous phase is discarded, and the organic phase is treated with 37% HCl under vigorous stirring until reaching pH<2. The resulting suspension is stirred for 30 minutes, then the precipitate is isolated by vacuum filtration and washed with THF. 58 kg of wet pure Givinostat are obtained.

The product is dried in oven at 30° C. under reduced pressure for 16 hours. 35 kg of dry pure Givinostat are obtained. HPLC purity analysis shows that the product does not contain any unknown impurities in amounts greater than 0.10% and has an overall purity greater than 99.5%.

Example 6 (Experiment TT259)

Synthesis of Givinostat According to the Process of the Invention (Step 1+Step 2)

Step 1: Synthesis of Intermediate (II)

100 g (0.2460 moles) di Intermediate (I) and 300 mL of dimethylformamide are charged into a 3 L reactor, previously dried and under an inert atmosphere. The suspension thus obtained is stirred at 20-25° C. for 30 minutes. 40 g (0.3362 moles) of thionyl chloride are added observing a slight exotherm, which is contained to maintain the reaction mixture at 20-25° C. The suspension obtained is kept at 20-25° C. for further 2 hours, then two vacuum cycles are performed, and pressure is restored with nitrogen, to remove the gases produced by the reaction. 2000 mL of THF are then added, keeping the mixture at 20-25° C. for 1 hour. The suspension is then filtered on a buchner and washed with 300 mL of THF. The wet product (133 g) is stored at 5° C. and used as-is.

Step 2: Synthesis of Givinostat 133 g of Intermediate (II) from STEP 1 and 960 mL of THF are charged into a 3 L reactor, previously dried and under an inert atmosphere. The suspension obtained is stirred and thermostated at 12-18° C. 160 g (2.424 moles) of 50% w/w hydroxylamine water solution are added to the suspension (the reaction is exothermic and the mixture temperature goes from 15° C. to 28° C.). It is then thermostated at 17-23° C. and kept in these conditions for 40'.

Then, keeping the same temperature, 1100 mL of deionized water are added, observing gradual dissolution of the precipitate. At the end, 220 g of 15% w/w HCl aqueous solution are added, until reaching a pH of the mixture of 1.2-1.8. The mixture is kept under stirring for 30 minutes at 17-23° C., then concentrated under reduced pressure while maintaining the internal temperature of 25° C. up to a residual volume of about 1400 mL. The pressure is then restored and 1000 mL of deionized water are charged. The mixture is then cooled to 7-13° C. and kept under stirring for 1 hour. The suspension is filtered by washing with 400 mL of deionized water acidified with 1.2 g of 37% HCl.

The wet filtrate is charged back into the reactor in which 5 kg of sodium bicarbonate, 1000 mL of deionized water and 1000 mL of THF are added. The mixture is stirred and heated to 47-53° C., keeping it in these conditions for 3 hours. The mixture is then cooled to 17-23° C. and the phases are allowed to settle. The separated aqueous phase is reextracted with 500 mL of ethyl acetate. The organic extracts are then combined and 200 mL of 37% HCl are added to these, under vigorous stirring, observing precipitation of the product. The mixture is kept under stirring for 30 minutes, then it is filtered and the panel washed with 400 mL of THF.

The wet filtrate is charged back into the reactor in which 5 kg of sodium bicarbonate, 1000 mL of deionized water and 1000 mL of THF are added. The mixture is stirred at 17-23° C., keeping these conditions for 30 minutes. 500 mL of ethyl acetate are then added to the mixture at 17-23° C., stirring for 15 minutes. The phases are allowed to settle and the separate organic phase is filtered on a 10 micron microfilter. Reactor and lines are then washed with a mixture of 120 mL of THF and 60 mL of ethyl acetate, and 200 mL of 37% HCl are added to the combined organic phases, observing precipitation of the product. The mixture is kept under stirring for 30 minutes, then it is filtered and the panel washed with 400 mL of THF. The product is discharged (157 g) and dried under vacuum (<50 mbar) at 25-35° C. for 15 hours. 107 g of final product are obtained.

Example 7 (Experiment TT267)

Synthesis of Givinostat According to the Process of the Invention (Step 1+Step 2)

A preparation of Intermediated (II), that is then transformed into Givinostat as described in Example 6, is repeated. At the end of the process 105 g of product are obtained.

Example 8 (Experiment TT287)

Synthesis of Givinostat According to the Process of the Invention (Step 1+Step 2)

100 g (0.2460 moles) of Intermediate (I) and 300 mL of dimethylformamide are charged into a 3 L reactor, previously dried and under an inert atmosphere. The suspension obtained is stirred at 20-25° C. for 30 minutes. 40 g (0.3362 moles) of thionyl chloride are then added observing a slight exotherm that is contained in order to maintain the reaction mixture at 20-25° C. The suspension obtained is kept at 20-25° C. for another 2 hours, then two vacuum cycles are performed, and pressure is restored with nitrogen, to remove the gases produced by the reaction. 2000 mL of toluene are then added, keeping the mixture at 20-25° C. for 1 hour. The suspension is then filtered on a buchner and washed with 300 mL of toluene. The wet product (133 g) is stored at 5° C. and used as it is. 133 g of Intermediate (II) from the described preparation and 960 mL of THF are charged into a 3 L reactor, previously dried and under an inert atmosphere. The obtained suspension is stirred and thermostated at 12-18° C. 160 g (2.424 moles) of 50% w/w hydroxylamine water solution are added to the suspension (the reaction is exothermic and the mixture temperature goes from 15° C. to 28° C.). Then, it is thermostated at 17-23° C. and kept in these conditions for 40'.

Then, keeping the same temperature, 1100 mL of deionized water are added while keeping the temperature at 17-23° C. and observing gradual dissolution of the precipitate. At the end, 220 g of 15% w/w HCl aqueous solution are added until reaching a pH of the mixture of 1.2-1.8. It is kept under stirring for 30 minutes at 17-23° C., then it is concentrated under reduced pressure while keeping the internal temperature at 25° C. until a residual volume of about 1400 mL is reached. Pressure is then restored and 1000 mL of deionized water charged. It is then cooled to 7-13° C. and kept under stirring for 1 hour. The suspension is filtered by washing with 400 mL of deionized water acidified with 1.2 g of 37% HCl.

The wet filtrate is charged back into the reactor in which 5 kg of sodium bicarbonate, 1000 mL of deionized water and 1000 mL of THF are added. The mixture is stirred and heated to 47-53° C., maintaining these conditions for 3 hours. The mixture is then cooled to 17-23° C. and the phases allowed to settle. The separated aqueous phase is reextracted with 500 mL of ethyl acetate. The organic extracts are then combined and 200 mL of 37% HCl are added to these, under vigorous stirring, observing precipitation of the product. The mixture is kept under stirring for 30 minutes, then it is filtered and the panel washed with 400 mL of THF.

The wet filtrate is charged back into the reactor in which 5 kg of sodium bicarbonate, 1000 mL of deionized water and 1000 mL of THF are added. The mixture is stirred at 17-23° C., keeping these conditions for 30 minutes. 500 mL of ethyl acetate are then added to the mixture at 17-23° C., stirring for 15 minutes. The phases are allowed to settle and the separate organic phase is filtered on a 10 micron microfilter. Reactor and lines are then washed with a mixture of 120 mL of THF and 60 mL of ethyl acetate, and 200 mL of 37% HCl are added to the combined organic phases, observing precipitation of the product. The mixture is kept under stirring for 30 minutes, then the panel is filtered and washed with 400 mL of THF. The product is discharged (157 g) and dried under vacuum (<50 mbar) at 25-35° C. for 15 hours. 107 g of final product are obtained.

Example 9

HPLC Method for Determining Givinostat Purity and Impurities Thereof

| Operative Conditions | |
|---|---|
| Chromatograph: | Shimadzu LC (or equivalent) |
| Detector: | UV |
| Column: | Halo C18-90 Å (250 × 2.1 μm (Code 95812-902, Advanced materials Technology) |
| Column Temperature | 25 ± 1° C. |
| Injection volume: | 5 μL |
| Mobile phase: | Phase A: 1000 mL Water + 1.23 g ammonium formate + 0.6 mL formic acid<br>Phase B: 1000 mL Methanol + 1.23 g ammonium formate + 0.6 mL formic acid<br>Sonicate phases for 10-15 min.<br>See gradient (table reported below) |
| Flow Rate: | 0.25 mL/min |
| Wavelength | UV 263/nm |
| Diluent | DMSO |

| Time (min) | Eluent A % (v/v) | Eluent B % (v/v) |
|---|---|---|
| 0 | 75 | 25 |
| 5 | 75 | 25 |
| 35 | 10 | 90 |
| 40 | 10 | 90 |
| 40.1 | 75 | 25 |
| 50 (end run) | 75 | 25 |

Sample Preparation

Weigh accurately about 20 mg of ITF2357 sample, transfer it into a 100 mL flask and fill up to volume with DMSO (conc. 0.20 mg/mL).

A typical chromatogram obtained by HPLC method according to the invention, on an ad hoc prepared mixture containing all typical impurities of the product, is shown in FIG. 1.

Example 11

Purity analysis for Givinostat obtained with the state of the art process (Example 2), with the process known in the art for STEP 1 and process of the invention for STEP 2 (Examples 3 and 4) and with the process of the invention both for STEP 1 and STEP 2 (Examples 6, 7 and 8)

TABLE 1

| Experiment | | RRT 0.93 ± 0.02 (17.6 min) | RRT 1 [Givinostat] (18.9 min) | RRT 1.08 ± 0.02 [Amide (Ia)] (20.4 min) | RRT 1.21 ± 0.02 (22.9 min) | RRT 1.27 ± 0.2 [Int.(I)] (24.0 min) | RRT 1.51 ± 0.02 (28.5 min) | RRT 1.75 ± 0.02 (33.1 min) |
|---|---|---|---|---|---|---|---|---|
| TT 180 | fine | 0.15 | 96.75 | — | 0.70 | 1.50 | — | 0.73 |
| Example 2 | coupling | | | | | | | |
| (state of the | crude | 0.21 | 96.84 | — | 0.43 | 1.81 | — | 0.57 |
| art) | pure | 0.03 | 98.83 | — | 0.23 | 0.73 | 0.06 | 0.06 |
| TT 177 | fine | 0.14 | 97.66 | — | 0.25 | 1.11 | | 0.68 |
| Example 3 | coupling | | | | | | | |
| (invention, | crude | 0.14 | 97.94 | — | 0.17 | 1.11 | — | 0.57 |
| only STEP 2) | pure | 0.02 | 99.35 | 0.02 | 0.09 | 0.42 | 0.05 | 0.05 |
| TT 183 | fine | 0.12 | 98.34 | — | 0.28 | 0.64 | — | 0.61 |
| Example 4 | coupling | | | | | | | |
| (invention, | crude | 0.12 | 98.43 | — | 0.20 | 0.68 | — | 0.54 |
| only STEP 2) | pure | — | 99.41 | — | 0.07 | 0.29 | 0.05 | 0.05 |
| TT 259 | fine | 0.13 | 98.97 | — | 0.49 | 0.36 | — | — |
| Example 6 | coupling | | | | | | | |
| (invention, | crude | 0.25 | 98.83 | — | 0.42 | 0.46 | — | — |
| STEP 1 + | pure | — | 99.62 | — | — | 0.38 | — | — |
| STEP 2) | | | | | | | | |
| TT 267 | fine | 0.11 | 98.98 | — | 0.51 | 0.40 | — | — |
| Example 7 | coupling | | | | | | | |
| (invention, | crude | 0.11 | 98.90 | — | 0.52 | 0.44 | — | — |
| STEP 1 + | pure | — | 99.61 | — | — | 0.39 | — | — |
| STEP 2) | | | | | | | | |
| TT 287 | fine | 0.12 | 98.86 | — | 0.47 | 0.55 | — | — |
| Example 8 | coupling | | | | | | | |
| (invention, | crude | 0.13 | 98.82 | — | 0.48 | 0.57 | — | — |
| STEP 1 + | pure | — | 99.57 | — | — | 0.43 | — | — |
| STEP 2) | | | | | | | | |

Table 1 shows, in particular, the relative retention times of Givinostat (RRT 1), amide metabolite (la) (RRT 1.08), intermediate (I) (RRT 1.27) and unknown impurities, evaluated by the HPLC analysis described in Example 9

The experiment TT 180 (Example 2) relates to repetition of the process used in the state of the art, while experiments TT 177 (Example 3) and TT 183 (Example 4) relates to experiments wherein the method of the present invention is applied with regards to STEP 2, where a 50% hydroxylamine aqueous solution is added to a solution of intermediate (II) produced according to the known art, dissolved in THF.

It is evident from the analysis of the purity data in Table 1 that the reverse addition order (hydroxylamine to intermediate (II)) compared to standard one (intermediate (II) to hydroxylamine) allows to obtain a reduction of all unknown impurities below 0.10% based on final reaction product. Vice versa, using the standard process, one impurity results to be well above the limit of 0.10%.

A further critical aspect to limit the impurities formation is the amount of water contained in the mixture containing intermediate (II) to which hydroxylamine is added, which must be limited within 0.5% based on the weight of the mixture. On the other hand, hydroxylamine addition time does not constitute a limitation while, unlike the state of the art method, the method of the present invention allows to operate at room temperature rather than at 5° C.

In Examples 6, 7 and 8 both the innovations of the present invention, regarding STEP 1 and STEP 2 have been applied. It will be clear from the values reported in the table that Givinostat is obtained with a purity greater than 99.5%, preferably equal or greater than 99.6%, and that no unknown impurities are detectable (detection limit of the method 0.02%).

The invention claimed is:

1. {6-[(diethylamino)methyl]naphthalen-2-yl}methyl [4-(hydroxycarbamoyl)phenyl]carbamate hydrochloride monohydrate, having an amount of any single unidentified impurity equal to or lower than 0.10 area % as determined by HPLC, wherein the unidentified impurity is selected from the group consisting of an unidentified impurity at a Relative Retention Time (RRT) of 0.93±0.02, an unidentified impurity at an RRT of 1.21±0.02, an unidentified impurity at an RRT of 1.51±0.02, and an unidentified impurity at an RRT of 1.75±0.02, wherein the RRT is determined using an HPLC method under the following operating conditions:

Stationary phase: support based on silica particles containing C18 alkyl chains and having a carbon load lower than 9% by weight;

Mobile phase A: Water buffered at pH 3.7-3.8

Mobile phase B: Methanol buffered at pH 3.7-3.8 using the following gradient elution method:

| Time (min) | Eluent A % (v/v) | Eluent B % (v/v) |
|---|---|---|
| 0 | 75 | 25 |
| 5 | 75 | 25 |
| 35 | 10 | 90 |
| 40 | 10 | 90 |
| 40.1 | 75 | 25 |
| 50 (end run) | 75 | 25 |

and subsequent detection of the {6-[(diethylamino)methyl]naphthalen-2-yl}methyl [4-(hydroxycarbamoyl)phenyl]carbamate hydrochloride monohydrate by means of a detector;

or having an amount of any single impurity other than intermediate (I) or amide (la) equal to or lower than 0.15%.

2. The {6-[(diethylamino)methyl]naphthalen-2-yl}methyl [4-(hydroxycarbamoyl)phenyl]carbamate hydrochloride monohydrate according to claim 1, having an amount of a single impurity other than intermediate (I) or amide (la) equal to or lower than 0.10%.

3. The {6-[(diethylamino)methyl]naphthalen-2-yl}methyl [4-(hydroxycarbamoyl)phenyl]carbamate hydrochloride monohydrate according to claim 1, having a purity equal to or greater than 99.6%.

4. The {6-[(diethylamino)methyl]naphthalen-2-yl}methyl [4-(hydroxycarbamoyl)phenyl]carbamate hydrochloride monohydrate according to claim 1, wherein the detector employed in the HPLC method is a detector of UV, MS or RID type.

5. The {6-[(diethylamino)methyl]naphthalen-2-yl}methyl [4-(hydroxycarbamoyl)phenyl]carbamate hydrochloride monohydrate according to claim 4, wherein the detector employed in the HPLC method is a 263 nm UV detector.

6. The {6-[(diethylamino)methyl]naphthalen-2-yl}methyl [4-(hydroxycarbamoyl)phenyl]carbamate hydrochloride monohydrate according to claim 1, wherein the buffer employed in the HPLC method is formate-formic acid buffer at pH 3.7-3.8.

7. The {6-[(diethylamino)methyl]naphthalen-2-yl}methyl [4-(hydroxycarbamoyl)phenyl]carbamate hydrochloride monohydrate according to claim 1, wherein the temperature employed in the HPLC method is 25±1° C.

8. The {6-[(diethylamino)methyl]naphthalen-2-yl}methyl [4-(hydroxycarbamoyl)phenyl]carbamate hydrochloride monohydrate according to claim 1, wherein the injection volume employed in the HPLC method is 5 μL.

9. The {6-[(diethylamino)methyl]naphthalen-2-yl}methyl [4-(hydroxycarbamoyl)phenyl]carbamate hydrochloride monohydrate according to claim 1, wherein the flow rate employed in the HPLC method is 0.25 mL/min.

10. The {6-[(diethylamino)methyl]naphthalen-2-yl}methyl [4-(hydroxycarbamoyl)phenyl]carbamate hydrochloride monohydrate according to claim 1, wherein DMSO is employed as a diluent for {6-[(diethylamino)methyl]naphthalen-2-yl}methyl [4-(hydroxycarbamoyl)phenyl]carbamate or a pharmaceutically acceptable salt in the HPLC method.

* * * * *